US00PP37398P3

(12) United States Plant Patent
Neu

(10) Patent No.: US PP37,398 P3
(45) Date of Patent: Apr. 28, 2026

(54) ***PELARGONIUM* PLANT NAMED 'KLEPZ24857'**

(50) Latin Name: *Pelargonium zonale*
Varietal Denomination: KLEPZ24857

(71) Applicant: KLEMM + SOHN GMBH & CO. KG, Stuttgart (DE)

(72) Inventor: Nina Neu, Weissach im Tal (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/187,663

(22) Filed: Apr. 23, 2025

(65) Prior Publication Data

US 2025/0351754 P1 Nov. 13, 2025

(30) Foreign Application Priority Data

May 13, 2024 (CH) ..... 24-3623

(51) Int. Cl.
*A01H 5/02* (2018.01)
*A01H 6/42* (2018.01)

(52) U.S. Cl.
USPC ..... Plt./329
CPC ..... *A01H 6/425* (2018.05); *A01H 5/02* (2013.01)

(58) Field of Classification Search
USPC ..... Plt./329
See application file for complete search history.

(56) References Cited

PUBLICATIONS https://www.mastergron.se/koncept-och-kampanj/arets-pelargon/2015-moonlight-violino/ (Year: 2015).*
https://germaniaseed.com/pdf/2025/2025_plant_supplemental.pdf (Year: 2024).*
https://online.plantvarieties.eu/publicConsultationDetails?registerId=20241384&denomination=Klepz24857 (Year: 2024).*

* cited by examiner

*Primary Examiner* — Shubo Zhou
*Assistant Examiner* — Zachariah Allan Kay
(74) *Attorney, Agent, or Firm* — Weatherly IP Solutions, LLC; Karen P. Bechtold; James M. Weatherly

(57) ABSTRACT

A new *Pelargonium* plant particularly distinguished by lavender flower color, weak zonation and dark colored leaves is disclosed.

1 Drawing Sheet

Genus and species: *Pelargonium zonale*.
Variety denomination: 'KLEPZ24857'.

CROSS REFERENCE TO RELATED APPLICATION

This patent application claims the benefit of priority from Plant Variety Protection Certificate No. 24-3623 as filed on May 13, 2024, in Switzerland, the contents of which are incorporated herein by reference for all it teaches and discloses.

BACKGROUND OF THE NEW PLANT

The present invention comprises a new and distinct variety of *Pelargonium*, botanically known as *Pelargonium zonale* and hereinafter referred to by the variety name 'KLEPZ24857'. 'KLEPZ24857' originated from a controlled cross in July 2019 in Juja, Kenya between the female *Pelargonium* variety 'PAC Greta' (patent status unknown) and the male *Pelargonium* variety 'PZ-2017-7321' (unpatented).

Seeds from the controlled cross were obtained. The seeds were sown and plants were grown for evaluation. A single plant was selected in June 2020 and subsequently named 'KLEPZ24857'. In July 2020 'KLEPZ24857' was first vegetatively propagated by vegetative stem cuttings in Stuttgart, Germany. 'KLEPZ24857' was found to reproduce true to type in successive generations of asexual propagation via stem cuttings in Stuttgart, Germany.

SUMMARY

The following are the most outstanding and distinguishing characteristics of this new variety when grown under normal horticultural practices in Stuttgart, Germany.

1. Lavender flower color
2. Weak zonation
3. Dark colored leaves

DESCRIPTION OF THE PHOTOGRAPH

This new *Pelargonium* plant is illustrated by the accompanying photograph which shows an overall view of the plant in a pot. The photograph is of an approximately 14-week-old plant grown indoors in Stuttgart, Germany. The photograph was taken indoors in Stuttgart, Germany in May 2023. The colors shown are as true as can be reasonably obtained by conventional photographic procedures.

DESCRIPTION OF THE NEW VARIETY

The following detailed descriptions set forth the distinctive characteristics of 'KLEPZ24857'. Data was collected on 14-week-old plants in Stuttgart, Germany under greenhouse conditions in March 2025. Color references are to The R.H.S. Colour Chart of The Royal Horticultural Society of London (R.H.S.), 5th edition (2007).

Classification:
- *Family*.—Geraniaceae.
- *Botanical*.—*Pelargonium zonale*.
- *Common*.—*Pelargonium*.
- *Designation*.—'KLEPZ24857'.

Parentage:
- *Female parent*.—'PAC Greta' (patent status unknown).
- *Male parent*.—'PZ-2017-7321' (unpatented).

Plant:
- *Form*.—Bushy.
- *Habit*.—Mounding.
- *Height* (*from top of soil*).—17.5 cm.
- *Width* (*horizontal plant diameter*).—17.5 cm.
- *Natural flowering season*.—March to October.
- *Propagation type*.—Vegetative by stem cuttings.
- *Time to produce a finished flowering plant*.—12 weeks.
- *Time to initiate and develop roots*.—4 weeks.
- *Root description*.—Fine, dense, white, RHS 158A.
- *Flower type*.—Zygomorphic.

Stems:
- *Quantity of stems per plant*.—2 to 5.
- *Color*.—RHS 144A.
- *Surface texture*.—Pubescent.
- *Stem form*.—Round.
- *Diameter*.—0.5 cm.
- *Length*.—4.0 cm to 6.0 cm.
- *Internode length*.—1.4 cm.
- *Anthocyanin*.—None.

Leaves:
- *Arrangement*.—Alternate.
- *Shape*.—Reniform.
- *Apex*.—Round.
- *Base*.—Overlapping.
- *Margin*.—Crenate.
- *Surface texture both surfaces*.—Pubescent.
- *Length*.—5.0 cm.
- *Width*.—7.0 cm.
- *Color*.—Upper surface: RHS N137A. Lower surface: RHS 137C.
- *Zonation*.—Yes, weak; distance to base: 1.0 cm; distance to margin: 1.2 cm.
- *Zonation color*.—RHS 147A.
- Depth of sinus.—2.0 cm.
- *Petiole*.—Length: 4.0 cm. Diameter: 0.2 cm. Color: RHS 144A.
- *Venation pattern*.—Palmate.
- *Venation color*.—Upper surface: RHS N137A. Lower surface: RHS 144A.

Inflorescence:
- *Lastingness of flowers on the plant*.—6 to 8 days.
- *Umbels*.—Quantity of umbels per plant: 3 to 5. Length: 9.5 cm. Diameter: 0.4 cm.
- *Individual florets of the umbel*.—Quantity of florets per umbel: 10 to 13. Depth: 1.2 cm. Diameter: 4.5 cm.
- *Fragrance*.—Absent.

Flower buds:
- *Cluster shape*.—Round.
- *Cluster size*.—Length: 1.5 cm. Width: 1.7 cm.
- *Surface texture*.—Pubescent.
- *Bud*.—Height: 0.6 cm. Width: 0.5 cm. Shape: Round. Apex: Acute. Base: Obtuse. Margin: Entire. Color: RHS 144A.

Petals:
- *Quantity per flower*.—5.
- *Shape*.—Spatulate.
- *Apex*.—Round.
- *Base*.—Obtuse.
- *Margin*.—Entire.
- *Length*.—2.6 cm.
- *Width*.—2.6 cm.
- *Surface texture*.—Upper surface: Smooth. Lower surface: Smooth.
- *Color of lobes*.—Upper lobes: Upper surface: RHS N80D basic color, RHS 84C at base. Lower surface: RHS 84D. Lower lobes: Upper surface: RHS N80D basic color. Lower surface: RHS 84D.
- *Markings*.—Slight color shift from margin to petal base of upper lobes.

Petaloids:
- *Quantity per flower*.—0 to 2.
- *Shape*.—Crippled and deformed linear.
- *Apex*.—Obtuse.
- *Base*.—Obtuse.
- *Margin*.—Entire.
- *Length*.—1.0 to 1.4 cm.
- *Width*.—0.5 cm.
- *Surface texture*.—Upper surface: Smooth. Lower surface: Smooth.
- *Color*.—Upper surface: RHS N80D. Lower surface: RHS 84D.

Sepals:
- *Number per flower*.—5.
- *Shape*.—Elliptic.
- *Apex*.—Acute.
- *Base*.—Obtuse.
- *Margin*.—Entire.
- *Surface texture*.—Upper surface: Smooth. Lower surface: Pubescent.
- *Color*.—Upper surface: 144A. Lower surface: 144A.
- *Length*.—0.6 cm.
- *Width*.—0.2 cm.

Pedicel:
- *Length*.—2.3 cm.
- *Diameter*.—0.2 cm.
- *Color*.—RHS 176A.
- *Surface texture*.—Pubescent.

Peduncle:
- *Length*.—10.0 cm.
- *Diameter*.—0.4 cm.
- *Color*.—RHS 176B.
- *Texture*.—Pubescent.

Reproductive organs:
- *Stamens*.—Quantity per flower: 4 to 8. Anther length: 0.2 cm. Filament length: 0.8 cm. Filament color: RHS N155D at base, RHS 65A at tip. Pollen amount: Medium. Pollen color: RHS 32A.
- *Pistils*.—Number: 1. Stigma color: RHS 61B. Style length: 0.2 cm. Style color: RHS 61B. Ovary arrangement: Central. Ovary color: RHS 176C. Ovary diameter: 0.2 cm. Ovary length: 0.5 cm. Ovary Texture: Pubescent.

Fruit and seed set: None observed to date.

Disease and pest/insect resistance: None observed to date.

COMPARISON WITH PARENTAL LINES AND KNOWN VARIETY

'KLEPZ24857' is distinguished from its parents as described in Table 1.

TABLE 1

| Comparison with Parental Lines | | | |
|---|---|---|---|
| Characteristic | 'KLEPZ24857' | Female parent | Male parent |
| Flower basic color | Lavender | Lavender pink | Lavender blue |
| Leaf zonation | Weak | None | Medium |

'KLEPZ24857' can be compared to the commercial variety 'Sunrise Lavina' (patent status unknown). Differences between the two varieties are described in Table 2:

TABLE 2

| Comparison with Similar Variety | | |
|---|---|---|
| Characteristic | 'KLEPZ24857' | 'Sunrise Lavina' |
| Flower color | Lavender | Lavender pink |
| Leaf color | Dark green | Green |

I claim:

1. A new and distinct variety of *Pelargonium* plant named 'KLEPZ24857' as illustrated and described herein.

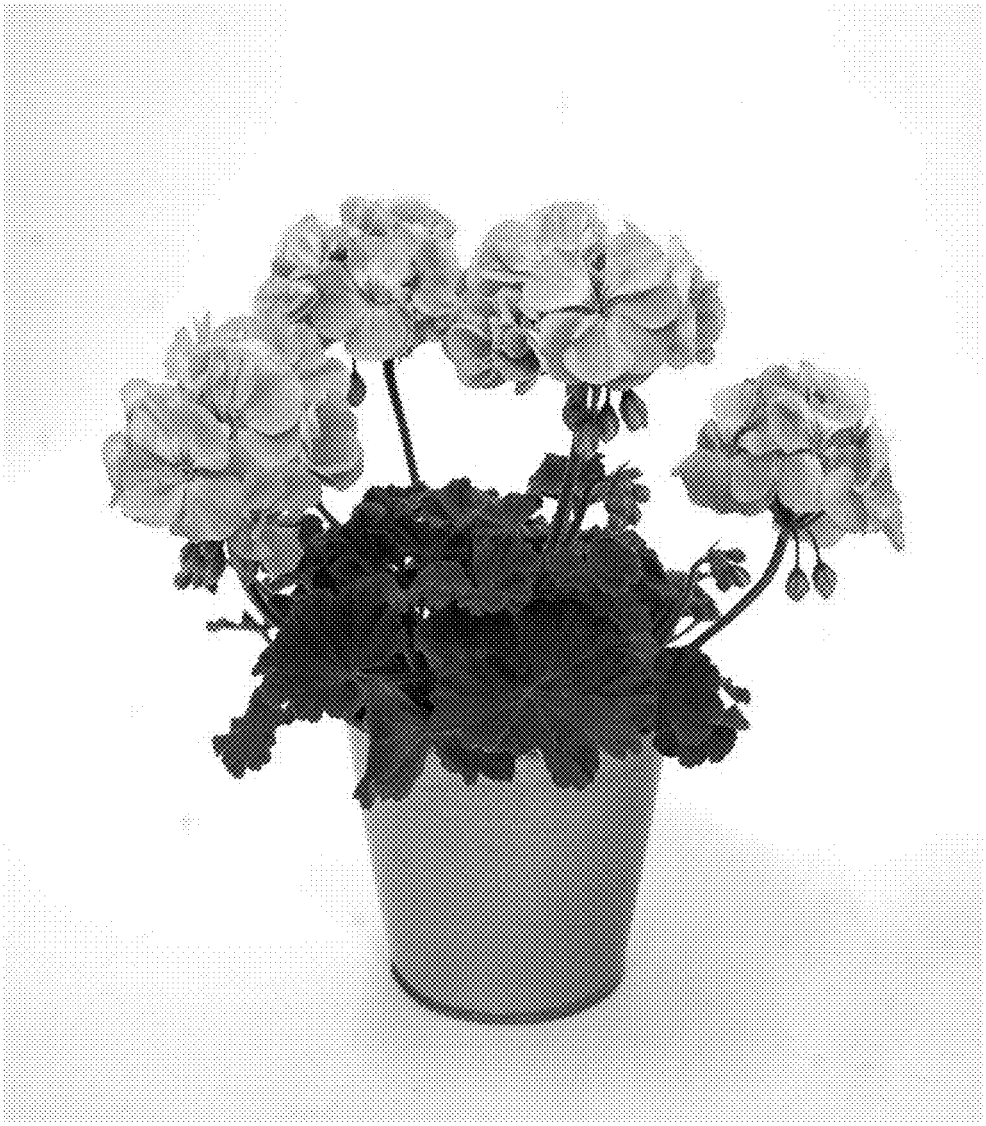

* * * * *